(12) United States Patent
Bernaert et al.

(10) Patent No.: US 8,637,093 B2
(45) Date of Patent: Jan. 28, 2014

(54) COMPOSITION AND USES THEREOF

(75) Inventors: Herwig Bernaert, Lebbeke-Wieze (BE); Leen Allegaert, Lebbeke-Wieze (BE)

(73) Assignee: Barry Callebaut AG, Zurich (CH)

( * ) Notice: Subject to any disclaimer, the term of this patent is extended or adjusted under 35 U.S.C. 154(b) by 271 days.

(21) Appl. No.: 12/907,347

(22) Filed: Oct. 19, 2010

(65) Prior Publication Data

US 2012/0263664 A1  Oct. 18, 2012

Related U.S. Application Data

(63) Continuation of application No. 12/104,799, filed on Apr. 17, 2008, now abandoned.

(51) Int. Cl.
*A61K 36/00* (2006.01)

(52) U.S. Cl.
USPC .......................... 424/725; 424/779; 424/401

(58) Field of Classification Search
None
See application file for complete search history.

(56) References Cited

U.S. PATENT DOCUMENTS

| | | | |
|---|---|---|---|
| 5,470,579 | A | 11/1995 | Bonte et al. |
| 5,554,645 | A | 9/1996 | Romanczyk et al. |
| 5,667,793 | A | 9/1997 | Cho et al. |
| 5,709,864 | A | 1/1998 | Andre et al. |
| 6,015,913 | A | 1/2000 | Kealey et al. |
| 6,159,451 | A | 12/2000 | Kim et al. |
| 6,313,128 | B1 | 11/2001 | Blanc-Ferras et al. |
| 7,122,574 | B2 | 10/2006 | Romanczyk et al. |
| 2003/0170199 | A1 | 9/2003 | Leclere et al. |
| 2003/0175234 | A1 | 9/2003 | Hernandez et al. |
| 2004/0096566 | A1 | 5/2004 | Lecoupeau et al. |
| 2004/0180102 | A1 | 9/2004 | Patt et al. |
| 2005/0008588 | A1 | 1/2005 | Candau et al. |
| 2005/0089592 | A1 | 4/2005 | Chevaux et al. |
| 2005/0186290 | A1 | 8/2005 | Cals-Grierson et al. |
| 2006/0045894 | A1 | 3/2006 | Brown et al. |
| 2006/0134179 | A1 | 6/2006 | Takagaki et al. |
| 2007/0148107 | A1 | 6/2007 | Sies et al. |
| 2007/0196298 | A1 | 8/2007 | Kostick et al. |
| 2007/0258920 | A1 | 11/2007 | Lecoupeau et al. |
| 2008/0038290 | A1 | 2/2008 | Renimel et al. |

FOREIGN PATENT DOCUMENTS

| | | |
|---|---|---|
| DE | 102004050563 | 4/2006 |
| EP | 0493151 | 7/1992 |
| EP | 1026164 | 8/2000 |
| EP | 1676606 | 7/2006 |
| FR | 2654935 | 5/1991 |
| FR | 2728563 | 6/1996 |
| FR | 2779645 | 12/1999 |
| FR | 2810242 | 12/2001 |
| FR | 2812873 | 2/2002 |
| FR | 2838055 | 10/2003 |
| FR | 2851916 | 9/2004 |
| FR | 2885050 | 4/2005 |
| JP | 2004262908 A | 2/2003 |
| WO | WO 96/10404 | 4/1996 |
| WO | WO 97/36597 | 10/1997 |
| WO | WO 98/09533 | 3/1998 |
| WO | WO 00/45769 | 8/2000 |
| WO | WO 01/35973 | 5/2001 |
| WO | WO 01/82889 | 11/2001 |
| WO | WO 01/91590 | 12/2001 |
| WO | WO 01/95872 | 12/2001 |
| WO | WO 02/14251 | 2/2002 |
| WO | WO 03/077668 | 9/2003 |
| WO | WO 03/079998 | 10/2003 |
| WO | WO 2004/006881 | 1/2004 |
| WO | WO 2004/080380 | 9/2004 |
| WO | WO 2005/027867 | 3/2005 |
| WO | WO 2005/115160 | 12/2005 |
| WO | WO 2006/000992 | 1/2006 |
| WO | WO 2006/029484 | 3/2006 |
| WO | WO 2006/072175 | 7/2006 |
| WO | WO 2006/117465 | 11/2006 |
| WO | WO 2006/117466 | 11/2006 |
| WO | WO 2007/076006 | 7/2007 |
| WO | WO 2007/082703 | 7/2007 |

OTHER PUBLICATIONS

Chocolate by the Numbers. Orange County Register. Feb. 8, 2007. pp. 1-4.

Gasser, P., et al., "Cocoa polyphenols and their influence on parameters involved in ex vivo skin restricting", *Journal of Cosmetic Science*, (2008) vol. 30, pp. 339-345.

Williams, S., et al., "Eating chocolate can significantly protect the skin from UV light", *Journal of Cosmetic Dermatology*, (2009) vol. 8, pp. 169-173.

*Primary Examiner* — Susan Hoffman
(74) *Attorney, Agent, or Firm* — Hoxie & Associates LLC

(57) ABSTRACT

A composition for topical application to the skin comprises a cocoa polyphenol extract in combination with an SUS-rich fat, wherein the cocoa polyphenol extract is present in an amount of less than 15% by weight based on the weight of the SUS-rich fat, and a cosmetically acceptable carrier. The composition and the extract that it contains may increase skin elasticity and thickness and/or have an anti-wrinkle effect, may cause the depigmentation of age spots, improve skin renewal and/or reduce skin dryness such as reducing discomfort of chapped hands.

9 Claims, 3 Drawing Sheets

COMPOSITION AND USES THEREOF

CROSS REFERENCE TO RELATED APPLICATIONS

This application is a continuation of U.S. application Ser. No. 12/104,799, filed Apr. 17, 2008, now abandoned, the contents of which are incorporated herein by reference.

BACKGROUND

This invention relates to compositions for topical application to the skin and to the use of the compositions and extracts that they contain for skin benefits.

Cosmetic compositions for topical application to the skin are used widely. The benefits that such topical compositions seek to provide are delivered directly to the skin and include, for example, relief from dryness, protection against sunlight and anti-ageing effects.

Cocoa that is used for the production of chocolate is made from the dried and partially fermented seeds of the cacao tree. The harvested cacao pods are opened, the pulp and cocoa beans are removed, and the rind is discarded. The pulp and beans are then piled in heaps, placed in bins, or laid out on grates for usually up to around 7 days, during which time the thick pulp liquefies as it ferments. The fermented pulp trickles away, leaving the cocoa beans behind to be collected, dried and further processed to make cocoa butter and cocoa powder. In some instances, the product is treated with alkali to reduce the acidity of the powder. Fermentation is important for the quality and flavour of the beans, which originally have a strong bitter taste. Unfermented or underfermented cocoa beans have a flavour similar to raw potatoes, are very susceptible to mildew and fungal growth, and therefore are not used in the manufacture of chocolate for food consumption. The cocoa bean without its shell is known as a "cocoa nib".

Cocoa is known to contain polyphenols and other biologically active compounds such as xanthines, including theobromine and caffeine.

Cocoa extracts containing polyphenols have been proposed for a number of uses. For example, WO 96/010404 describes cocoa extracts containing proanthocyanidins that are said to be anti-neoplastic. U.S. Pat. No. 7,122,574 discloses polyphenol-containing cocoa extracts that can be used for treating hypertension. WO 03/079998 states that cocoa extracts containing polyphenols can be used in the treatment of diseases involving defective gap junctional communication.

US20070148107 describes a method of reducing UV-induced skin erythema and/or photoaging in a subject in need thereof comprising orally administering to the subject a composition comprising an effective amount of a cocoa component.

FR2885050A1 discloses a slimming cosmetic and/or pharmaceutical composition for the treatment of the adipocytes of skin which comprises a cocoa extract containing polyphenols. There is no mention of how the cocoa extract is obtained.

US20060134179 relates to a health food product comprising proanthocyanidins, ascorbic acid or a derivative thereof, and L-cysteine or a derivative thereof. The product is said to provide an excellent beautification (skin-beautifying) effect.

WO 02/14251 describes a method for obtaining cocoa bean polyphenol extracts by solvent extraction of fresh cocoa beans. The extracts have cosmetic, food and therapeutic uses and may contain increased levels of beta-sitosterol.

US 2003/0170199 discloses cocoa extracts containing polyphenols that can be used in cosmetic compositions.

WO 2006/117465 relates to the use of certain cocoa polyphenol extracts for controlling skin pigmentation.

R-A-2838055 A1 describes the use of an extract of cacao for modulating the formation of pro-inflammatory agents following exposure to harmful chemicals. The extract is obtained by the solvent extraction of defatted cocoa powder.

WO2004/080380 relates to the use of at least one catechuic polyphenol for a compound or a preparation for stimulating the natural pigmentation of skin or skin integument.

Our copending applications GB 0719543.1 and GB 0801401.1 relate to the oral administration of cocoa polyphenol extracts and cocoa powders to obtain skin benefits.

Despite the effectiveness of compositions such as those described in WO 02/1425, there remains a need to improve the properties of cosmetic compositions for topical application. Also, there is a desire to improve the efficacy and/or performance of cosmetic compositions such as those comprising cocoa polyphenol extracts.

BRIEF SUMMARY OF THE INVENTION

According to the invention, there is provided a composition for topical application to the skin comprising a cocoa polyphenol extract in combination with an SUS-rich fat, wherein the cocoa polyphenol extract is present in an amount of less than 15% by weight based on the weight of the SUS-rich fat, and a cosmetically acceptable carrier.

The invention also provides the use of a cocoa polyphenol extract in a cosmetic composition for topical application, for increasing skin elasticity and thickness and/or an anti-wrinkle effect.

Further provided by the invention is the use of a cocoa polyphenol extract in a cosmetic composition for topical application, for the depigmentation of age spots.

Also provided by the invention is the use of a cocoa polyphenol extract in a cosmetic composition for topical application, for the improvement of skin renewal.

Yet further provided by the invention is the use of a cocoa polyphenol extract in a cosmetic composition for topical application, for reducing skin dryness such as reducing discomfort of chapped hands.

The invention also provides a method for increasing skin elasticity and thickness and/or reducing skin wrinkles comprising the topical application of a cosmetic composition comprising an effective amount of a cocoa polyphenol extract to a subject in need thereof. Further provided by the invention is a method for the depigmentation of age spots comprising the topical application of a cosmetic composition comprising an effective amount of a cocoa polyphenol extract to a subject in need thereof.

Also provided by the invention is a method for improving skin renewal comprising the topical application of a cosmetic composition comprising an effective amount of a cocoa polyphenol extract to a subject in need thereof.

Yet further provided by the invention is a method for reducing skin dryness such as reducing discomfort of chapped hands comprising the topical application of a cosmetic composition comprising an effective amount of a cocoa polyphenol extract to a subject in need thereof.

Preferably, in the methods and uses of the invention: the cocoa polyphenol extract is obtainable by the extraction of non-defatted cocoa beans which have not been fermented or have been allowed to ferment for no more than three days; and/or or the cocoa polyphenol extract is provided in combination with an SUS-rich fat.

DETAILED DESCRIPTION OF THE INVENTION

Figure 1A:
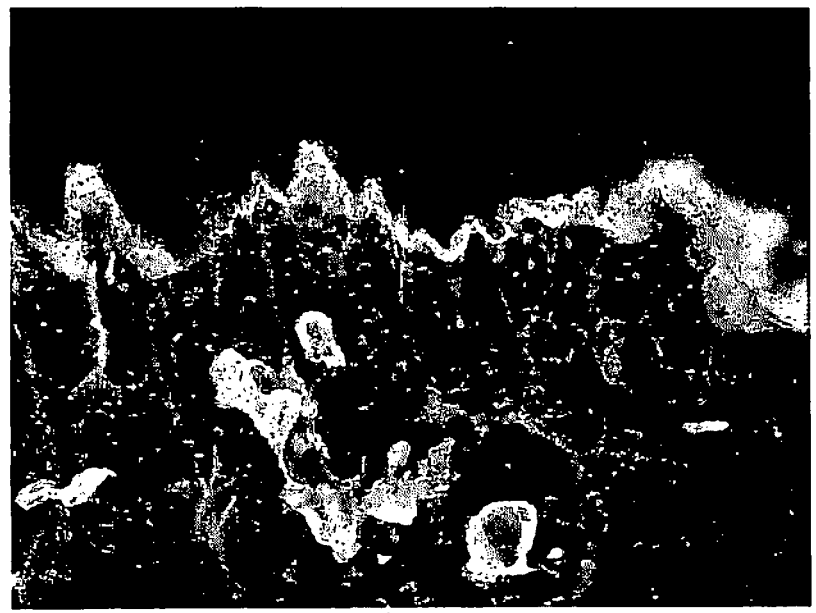
FIG. 1 illustrates the effect on collagen IV as detailed in Example 1.

The present invention is based on the surprising finding of a synergistic effect between cocoa polyphenol extracts and SUS-rich fat in providing benefits to the skin. In particular, the effect is especially surprising at relatively low levels of the cocoa polyphenol extract compared to the amount of SUS-rich fat.

It has been found that the topical application of SUS-rich fat together with certain cocoa polyphenol extracts can induce one or more of: an increase of the epidermal thickness; a denser collagen in the papillary dermis (part of the dermis close to the epidermis), for example an increase in collagen type l and/or type lll (dermal fibrillary collagens) and/or type IV (unfibrillary collagen present at the dermal-epidermal junction (DEJ)), typically around cutaneous annexes; and an increase of neutral glycosaminoglycans (GAGs), for example close to the DEJ. The composition can also induce an increase of the acid GAGs, for example in the epidermal inter-cell spaces and in the papillary dermis.

In the skin, neutral GAGs are observed close to the basal membranes such as the epidermis/dermis bond, around blood vessels and cutaneous annexes. They may be visualized, after alcian blue-P.A.S. specific colouration, as a pink band more or less dense and more or less regular. Acid GAGs are also present in the skin and are observed in the epidermal inter-cell spaces and in the dermis which sticks to thin fibers in the inter-collagen bundle spaces. After specific colouration, they are visualized in blue.

The compositions of the invention may be beneficial for cutaneous structure because they may increase epidermal thickness and/or strengthen the epidermal dermal bond (which is an important zone in the epidermal dermal bond).

GAGs have an important activity in growth factor stabilization and concentration. Acid GAGs, essentially hyaluronic acid, are very involved in the hydration process. In the dermis, this hyaluronic acid improves the skin plasticity. GAGs may also increase the epidermal thickness with a decrease of the cellular differentiation inducing an improvement of the skin surface. GAGs can also stimulate fibroblasts which may express dermal structure components, for example increasing collagen, including collagen l and lll. These activities may contribute to strengthening the mechanical dermal resistance.

The application of cocoa polyphenols incorporated in SUS-rich fat, on the human skin, may contribute to strengthening the epidermal and dermal structures producing a supple and younger skin.

The cosmetic compositions of the invention comprise the cocoa polyphenol extract, SUS-rich fat and a cosmetically acceptable carrier.

The extracts that are used in the invention are preferably prepared from non-defatted cocoa beans which have not been fermented or have been fermented for a short time, such as less than three days.

The extract that is used in the compositions of the invention is typically a brown-coloured, free-flowing powder. Usually, the extract will have no noticeable odour.

The extract of the invention preferably has a polyphenol content of at least 40% by weight, such as at least 45% by weight (based on the weight of the extract). The upper limit for the polyphenol content is typically about 70% by weight. Thus, preferred amounts of polyphenol include from 30% to 70%, from 35% to 70%, from 40% to 70%, from 45% to 65% and from 45% to 60%, the percentages being by weight of the extract. The percentages of polyphenols are preferably expressed as gallic acid equivalents, according to the Folin-Ciocalteu method (e.g., as described in Singleton V L, Orthofer R, Lamuela-Raventos R M. Analysis of total phenols and other oxidation substrates and antioxidants by means of Folin-Ciocalteu reagent. Meth Enzymol 1999; 99: 152-178).

Polyphenols in the extracts that are used in the invention typically comprise monomers and oligomers. Preferably, the extracts of the invention comprise up to 10% by weight of each of monomers, dimers, trimers, tetramers, pentamers, hexamers, heptamers, octamers, nonamers and decamers, and higher oligomers in an amount of up to 15% by weight. More preferably, extracts of the invention comprise, by weight of the extract, 5-10% monomers (preferably including at least 5% epicatechin), 5-10% dimers, 5-10% trimers, 2-8% tetramers, 2-8% pentamers, 2-8% hexamers, 0.5-5% heptamers, 0.1-4% octamers, 0.1-3% nonamers and 0.05-2% decamers, and 5-12% higher oligomers.

Extracts useful in the invention may contain xanthines (preferably methylxanthines), such as caffeine and theobromine. Caffeine may be present together with theobromine, typically at a weight ratio of theobromine to caffeine in the range of from 20:1 to 5:1. In one embodiment of the invention, the theobromine content is at least 5% by weight, and preferably from 5 to 11% by weight. In this embodiment, the composition preferably has a weight ratio of from 7:1 to 12:1 polyphenol:theobromine. In an alternative embodiment, the extract may be treated, for example with supercritical carbon dioxide, to lower the theobromine content and the content of other xanthines that may be present. For example, a method for lowering the content of theobromine in extracts of this type is described in Example 2.3 of WO 2007/082703, the contents of which are incorporated herein by reference. In this alternative embodiment, the extract has a theobromine content of less than 5% by weight, such as less than 4.5% by weight, for example from 0.1 to 4% by weight.

The extracts used in the invention are preferably prepared from cocoa beans that are non-defatted and have not been fermented or have been allowed to ferment for no more than three days. The cocoa beans will typically not have been roasted. Thus, the cocoa beans that are used as the starting material for the production of the extracts of the invention are very different from the cocoa beans that are used to produce cocoa powder and chocolate. Typically, the extracts are prepared from cocoa nibs which are deshelled cocoa beans that are unfermented and non-roasted.

The cocoa beans are preferably obtained by a process that comprises: harvesting and hulling cocoa beans; preventing fermentation of the beans or allowing the beans to ferment for no more than three days (more preferably less than two days, even more preferably less than one day) before halting the fermentation process by drying.

The fat content of the non-defatted cocoa beans, or of the cocoa nibs, that are used in the invention, is typically greater than 30% by weight, more preferably greater than 35% by weight, even more preferably greater than 40% by weight, such as greater than 45% by weight; for example, greater than 50% by weight.

Extracts of the invention are preferably obtainable by solvent extraction of the cocoa beans. The solvent is preferably selected from C1 to C6 alcohols or C1 to C6 ketones, and mixtures thereof, optionally in admixture with water, such as, for example, ethanol, acetone, 2-butanol, 2-propanol and mixtures thereof, optionally in admixture with water. A particularly preferred solvent comprises a mixture of water and acetone in a weight ratio of water:acetone of from 1:1 to 1:9. Preferably, solvent extraction is carried out using a counter current process for a time and at a temperature to achieve the desired degree of extraction, typically from one hour to 2 days at from 20 to 60° C. After extraction, the liquid solvent extract is typically evaporated to remove a part of the solvent and then spray dried. To improve its solubility, the extract powder is preferably agglomerated in a fluidised bed. The xanthine (and theobromine) content of the extract may be reduced by extraction with super-critical carbon dioxide after the solvent has been removed.

Processes that may be used for producing the extracts of the invention are described in WO 2007/082703 and WO 02/14251, the contents of which are incorporated herein by reference.

Extracts of the invention preferably comprise less than 2% by weight phenylethylamine. Extracts of the invention may comprise other components derived from the cocoa beans such as protein and sugars. Typically, the extracts comprise from 15 to 40% by weight protein, such as from 20 to 30% by weight protein. The extracts may comprise from 2 to 12% by weight sugars, such as from 4 to 10% by weight sugars. Again, the percentages are based on the weight of the extract.

The extracts of the invention comprise cocoa fats. The term "fats" as used in this context includes lipid material in cocoa beans such as sterols, lipids and phospholipids, as well as mono-glycerides and di-glycerides. Without wishing to be bound by theory, it is believed that these one or more components of the cocoa fats contribute to the beneficial physiological effects of the extracts of the invention. Preparing the extracts of the invention from cocoa beans which have not been defatted or fermented for any substantial length of time increases the amounts of these fat components compared to extracts from defatted beans or beans that have been fermented.

Preferably, the extracts of the invention comprise from 0.1 to 10% by weight of cocoa fats, such as from 0.2 to 8%, or from 0.3 to 7%, or from 0.5 to 5%, or from 0.7 to 3%, by weight of cocoa fats, based on the weight of the extract. Preferably, the cocoa fats are non-triglyceride lipids.

An example of a preferred extract of the invention comprises:
(i) from 35 to 70% by weight cocoa polyphenols;
(ii) from 1 to 10% by weight xanthines;
(iii) less than 2% by weight phenylethylamine; and
(iv) from 0.1 to 10% by weight of cocoa fats.

One or more extracts of the invention may be admixed to form a mixed extract composition.

It will be appreciated that the term "extract" means that the material has been at least partially separated from some or all of the components with which it naturally occurs in cocoa.

An SUS-rich fat is present in the compositions of the invention. The term "SUS" is standard in the art and refers to triglyceride fats having S groups at the 1- and 3-positions of the glycerol moiety and U groups at the 2-position of the glycerol moiety. S represents saturated C12 to C24 straight chain fatty acyl, such as the acyl group of palmitic acid, and U represents C12 to C24 unsaturated straight chain fatty acyl, such as the acyl group of oleic acid. The SUS-rich fat typically comprises at least 75% by weight triglycerides. SUS-rich fats comprise at least 40%, more preferably at least 50%, even more preferably at least 60% by weight of SUS triglycerides. Suitable SUS-rich fats include cocoa butter, cocoa butter fractions, palm oil fractions, shea fat, shea fat fractions, sal fat, sal fat fractions, and mixtures thereof. Preferably, the SUS-rich fat is cocoa butter. Cocoa butter is a commercially available product and is obtainable from cocoa by known methods.

Compositions of the invention may be prepared by a method comprising providing a cocoa polyphenol extract and combining the extract with SUS-rich fat, wherein the cocoa polyphenol extract is present in an amount of less than 15% by weight based on the weight of the SUS-rich fat. A cosmetically acceptable carrier is incorporated into the composition with the extract or the SUS-rich fat prior to the combining step or after the combining step. Preferably, the combined extract and SUS-rich fat is formulated with a cosmetically acceptable carrier.

The ratio of SUS-rich fat to cocoa polyphenol extract in the compositions of the invention is different from that present in conventional cocoa liquors and materials.

Preferably, the cocoa polyphenol extract is present in the compositions of the invention in an amount of from 0.01% to 13% by weight based on the weight of the SUS-rich fat, more preferably from 0.05% to 5% by weight or from 0.1% to 1.0% by weight based on the weight of the SUS-rich fat, such as from 0.1% to 13% by weight or from 8% to 12%, for example about 10% by weight based on the weight of the SUS-rich fat.

The SUS-rich fat is preferably present in compositions of the invention in an amount of from 1% to 80% by weight, more preferably from 2% to 40% by weight such as from 3% to 20% by weight or 4% to 10% by weight, based on the total weight of the composition.

The composition of the invention is suitable for topical application to the skin and thus contains a cosmetically acceptable carrier i.e., a carrier that is compatible with the skin. The skin is typically mammalian skin, preferably human skin. The compositions are typically applied by the end user of the product directly to his or her skin.

Cosmetic compositions of the invention are for topical use and comprise the cocoa polyphenol extract in combination with SUS-rich fat, and a cosmetically acceptable carrier. The compositions may consist of, or consist essentially of, the cocoa polyphenol extract, SUS-rich fat, a cosmetically acceptable carrier, and optionally one or more adjuvants selected from preservatives, antioxidants, solvents, fragrances, fillers, screening agents, pigments, odour absorbers, viscosity enhancers, thickeners, gelling agents, pH modifier and colouring agents.

The composition may be formulated in any way normally used in cosmetics, and it may, for example, be in the form of a dispersion, suspension or emulsion. Typically, dispersions, suspensions and emulsions comprise at least an aqueous phase and an oil phase. For example, an emulsion may be an oil in water (O/W emulsion) or water in oil (W/O emulsion), or it may be a triple emulsion (W/O/W or O/W/O emulsion) or a vesicular dispersion of the ionic and/or nonionic type. These compositions can be prepared according to conventional methods.

Cosmetically acceptable carriers suitable for use in the compositions of the invention may be single components or mixtures of two or more components. Suitable carriers are those that are common in cosmetics, including, for example, water, oils and/or fats, solvents, emulsifiers, co-emulsifiers, hydrophilic and lipophilic gelling agents, and hydrophilic and lipophilic active agents.

The solvent is chosen as a function of the components used and the administration form envisaged. Solvents include, for example, propylene glycol, an alcohol, in particular ethanol, or a diethylene glycol ether.

When the cosmetic composition is a dispersion, suspension or emulsion, the proportion of the oil phase may range from 5% to 80% by weight such as from 5% to 50% by weight relative to the total weight of the composition. The emulsifier and co-emulsifier are preferably present in the composition in an amount ranging from 0.3% to 30% by weight such as from 0.5% to 20% by weight relative to the total weight of the composition. The aqueous phase preferably constitutes from 10% to 80% by weight of the composition and the remainder is represented by the essential components, namely the cocoa extract and SUS-rich fat, and the optional components.

Oils which may be used in the invention in addition to the SUS-rich fat include, for example, mineral oils, oils of plant origin, oils of animal origin and silicone oils. Fatty alcohols, fatty acids, esters of fatty acids (where the term "fatty" refers to C12-C24 straight chain alkyl or alkenyl compounds) and waxes may also be used as fats. Preferred oils include jojoba oil, corn oil, liquid petroleum jelly, hydrogenated coconut oil, safflower oil, saturated fatty acid glycerides, stearic acid, palmitic acid, octyl stearate, glyceryl palmitate, octyl palmitate, a capric or caprylic acid triglyceride, 2-octyldodecanol, lanolin alcohol, polyethylene glycol, 2-ethylhexyl adipate, or silicone oils such as methylphenylpolysiloxane, dimethicone, cyclomethicone, cyclomethicone/dimethicone copolyol or phenyl trimethicone.

Emulsifiers and co-emulsifiers that may be used include, for example, carboxyvinyl polymers of high molecular weight (for example Carbopol®), polysorbates (for example Tween 20® or Tween 60), sorbitan esters and in particular a sorbitan monostearate, tristearate, monopalmitate or laurate. Other emulsifiers such as various stearic acid or palmitic acid derivatives, for example PEG-100 stearate, stearic acid or palmitic acid mono- or diglycerides, a self-emulsifying propylene glycol stearate, or polyglyceryl 2-sesquioleate, polyoxyethylene cetyl ether, a siloxane polyglucoside or an emulsifiable silicone may also be used. Mixtures of nonionic emulsifiers may also be used.

The viscosity enhancers optionally used in the compositions of the invention may be chosen from various acrylic acid polymers, cellulose gums, silica, carboxyvinyl polymers, for example Carbomer, magnesium aluminium silicate, and the colloidal silica sold under the brand name Aerosil 200® or a crosslinked polyacrylic acid such as Carbopol 940® may be used, for example.

The gelling agents or thickeners may be chosen, for example, from polyacrylamides, acrylates, for instance Pemulen®, cellulose derivatives, for instance hydroxypropyl cellulose, or natural gums.

The compositions of the invention optionally further comprise one or more further active components. Active components include, for example, UVA-active and UVB-active photoprotective agents, desquamating agents, moisturizers, emollients, agents for stimulating collagen synthesis, such as soybean protein hydrolysates, agents for stimulating elastin synthesis and/or for inhibiting collagen degradation, agents for stimulating glycosaminoglycan synthesis, agents for stimulating fibroblast and/or keratinocyte proliferation or for stimulating keratinocyte differentiation, dermo-relaxants such as sapogenins and natural extracts, antipollution agents and/or free-radical scavengers, agents that act on the capillary circulation and agents that act on the energy metabolism of cells. Specific active components include, for example, tocopherol, vitamin A (retinol), retinoic acid and bactericides. The moisturizers used in the compositions of the invention may be chosen, for example, from a polyol, sorbitol, maltitol, pentaerythritol, polyglyceryl acrylates and methacrylates, glycerol or glycerol derivatives. Emollients such as an alkyl malate, isohexadecane, capric or caprylic acid triglycerides, etc. may also be added.

Cosmetic compositions may optionally comprise one or more adjuvants, preferably selected from one or more of preservatives, antioxidants, solvents, fragrances, fillers, screening agents, pigments, odour absorbers, viscosity enhancers, thickeners, gelling agents, pH modifiers and colouring agents. The at least one adjuvant is typically present in an amount ranging, for example, from 0.01% to 20% by weight based on the total weight of the composition.

The pH of the composition is preferably between 5.5 and 7.5 and may be adjusted, depending on the particular composition, by adding a pH modifier, for example an acid such as citric acid or a base such as sodium hydroxide.

The composition may be in a form conventionally used for topical application, for example in the form of a gel, a lotion, an emulsion (in particular a cream or a milk), a mask, a stick, a wipe or a pomade, containing common compatible and pharmaceutically acceptable excipients and supports. These topical administration forms are prepared by the known techniques, and for example, in the case of a cream, by dispersing a fatty phase in an aqueous phase to obtain an oil-in-water emulsion, or conversely to prepare a water-in-oil emulsion.

Compositions of the invention will typically be packaged, for example in a container such as a tube, bottle, sachet, tub or jar, and will generally be labelled for cosmetic use.

The compositions of the invention are typically adapted for topical application to the skin preferably one, two or more than two, typically up to four times daily, although they may be used more or less frequently than this. The compositions may provide one or more benefits, including increasing skin elasticity and/or thickness, depigmenting age spots, improving skin renewal and reducing dryness, such as discomfort of chapped hands. The compositions may have an anti-wrinkle effect. Surprisingly, the effects achieved by using the cocoa polyphenol extract in combination with SUS-rich fat are greater than expected and are significantly better than when using the extract alone.

The listing or discussion of an apparently prior-published document in this specification should not necessarily be taken as an acknowledgement that the document is part of the state of the art or is common general knowledge.

The following non-limiting examples illustrate the invention and do not limit its scope in any way. In the examples and throughout this specification, all percentages, parts and ratios are by weight unless indicated otherwise.

EXAMPLES

Cocoa Polyphenol Extract

The cocoa polyphenol extract used in the examples was prepared as follows.

An extract was prepared by extraction of cocoa nibs (deshelled cocoa beans unfermented and non-roasted) in a counter-current process with the use of a 70/30 mixture of acetone/water. The liquid extract is evaporated and then spray-dried. To improve solubility, the extract powder is agglomerated in a fluidised bed.

The extract had the following composition (% by weight):

| | |
|---|---|
| Polyphenols | 47.5 |
| Ash | 4.3 |
| Xanthines | 6.9 |
| Moisture | 3.5 |

-continued

| | |
|---|---|
| Fat | 1.5 |
| Sugars | 6.1 |
| Proteins | 24.5 |
| Fibres | 5.5 |
| Others | 0.2 |

The polyphenol content (as % by weight of total polyphenols) was as follows:

| | |
|---|---|
| Monomers | 8.2 |
| | (7.15% epicatechin and 1.04% catechin) |
| Dimers | 7.1 |
| Trimers | 7.3 |
| Tetramers | 4.4 |
| Pentamers | 3.8 |
| Hexamers | 3.5 |
| Heptamers | 1.4 |
| Octamers | 0.9 |
| Nonamers | 1.1 |
| Decamers | 0.4 |
| Higher | 9.5 |

No gallic acid or gallic acid derivatives were detected.

Example 1

In Vitro Experiment

Explant Preparation

Explants were prepared from abdominal plasties of Caucasian women aged 39-68 years old. Explants of around 10 mm in diameter were prepared with a circular scalpel and put in survival in classical cell culture conditions for 11 days. They were distributed in 4 batches of 6 explants each and one of 3 explants on day 0 as follows:
  I. Blank batch, non treated
  II. Formula A batch, treated by topical application with the tested formula A at 0.5% of polyphenol extract
  III. Formula B batch, treated by topical application with the tested formula B at 0.5% of polyphenol extract and 5% of cocoa butter
  IV. And three explants taken off at day 0, batch T0.

Tested Products

Formula A at 0.5% of cocoa polyphenol extract
Formula B at 0.5% of cocoa polyphenols and 5% of cocoa butter Explants were treated by topical application with 2 mg by explant. Products were applied on day 0 (D0), day 1 (D1), D2, D4, D6, D8 and D10, spread with a small spatula.

Samples for Histology
  On day 0, the explants of batch T0 were taken off and 3 explants of each batch have been taken off on each time (at D5 and D11). Explants were cut in two parts, one half was frozen at −75° C. for different immunostaining, and the other half was fixed in ordinary Bouin solution for general morphology staining After 48 h ordinary Bouin fixation, explants were dehydrated and embedded in paraffin in a Leica 1020 automat. 5 μm thick sections were realized with a Minot type microtome Leica RM 2125. They were stuck.
  Frozen sections were cut at 7 μm in a Leica CM 3050 cryostat and stuck on silanized histological glass slides.

Histological Study

General Morphological:
  The general morphology was carried out on paraffinized sections according to Masson's trichrom staining.

Collagen I Immunostaining
  The immunostaining was carried out on frozen sections with an anti-collagen-I, polyclonal (from Monosan ref PS047) with a biotin/streptavidin enhancement system and revealed by FITC. Nucleus was stained with propidium iodide.

Collagen III Immunostaining
  The immunostaining was carried out on frozen sections with an anti-collagen-III, polyclonal (from SBA ref 1330-01) with a biotin/streptavidin enhancement system and revealed by DAB. Nucleus was stained with Masson's hemalun.

Collagen IV Immunostaining
  The immunostaining was carried out on frozen sections with an anti-collagen IV, polyclonal (from SBA ref 1340-01) with a biotin/streptavidin enhancement system and revealed by FITC. Nucleus was stained with propidium iodide.

Microscopic Observation
  Microscopic observation was carried out with a Leica DMLB optical microscope. Photos were taken by Sony camera tri CCD with an IM 1000 Leica system.

Figure 1B:
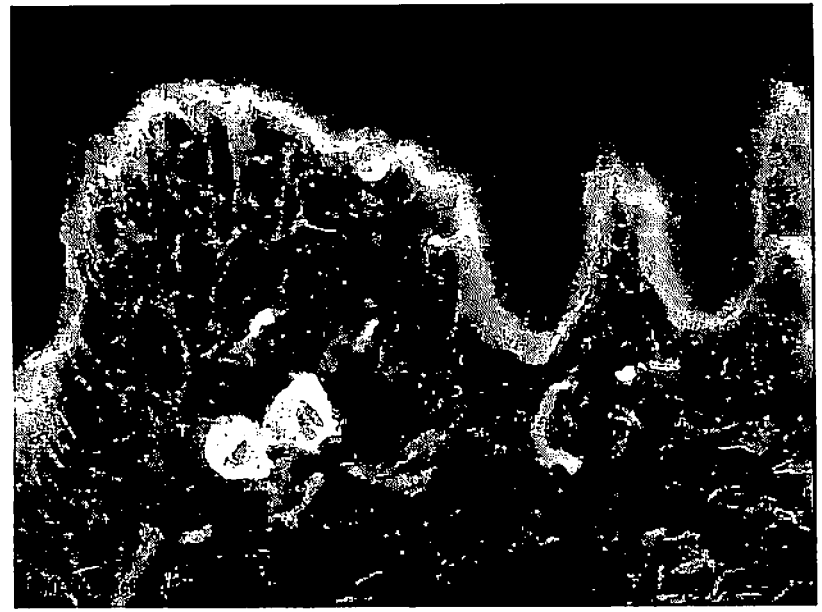
Figure 2A:
FIG. 2 illustrates the effect on neutral GAGs as detailed in Example 1.
Figure 2B:

Results
  In these operating conditions and according to these results:
  No effect was observed in the untreated group.
  The formula containing 0.5% of polyphenols induced:
    No epidermal thickness increase after 11 days.
    No collagen density increase in the papillary dermis after 11 days.
    A clear neutral GAGs induction after 5 days.
    A clear collagen l induction after 11 days.
    No collagen lll induction after 11 days.
    A clear collagen IV induction after 11 days.
  The formula containing 0.5% of polyphenols with 5% cocoa butter induced:
    A slight epidermal thickness increase after 11 days.
    A slight collagen density increase in the papillary dermis after 11 days.
    A very clear neutral GAGs induction after 5 days.
    A very clear collagen l induction after 11 days.
    A very slight collagen lll induction after 11 days.
    A very clear collagen IV induction after 11 days.
  The effect on collagen IV after 11 days is shown in FIG. 1. FIG. 1A is the composition comprising 0.5% polyphenol extract and FIG. 1B is the composition containing 0.5% of polyphenols with 5% cacao butter.
  The effect on neutral GAGs after 11 days is shown in FIG. 2. FIG. 2A is the composition comprising 0.5% polyphenol extract and FIG. 2B is the composition containing 0.5% of polyphenols with 5% cacao butter.

Example 2

Age Spot Depigmentation

An objective measurement was carried out on the effect of a skin cream containing cocoa polyphenols and cocoa butter on skin depigmentation of age spots.

The skin cream had the following formulation:

| Name | Weight % |
|---|---|
| Mineral oil | 6.00 |
| PPG-15 stearyl ether | 6.00 |
| Theobroma cocoa seed butter | 5.00 |

-continued

| Name | Weight % |
|---|---|
| Cyclopentasiloxane | 4.00 |
| Glycerin | 4.00 |
| Steareth-2 | 3.00 |
| Steareth-21 | 3.00 |
| Polacrylamide | 0.80 |
| Cocoa polyphenol extract | 0.50 |
| Phenoxyethanol | 0.44 |
| C13-14 isoparaffin | 0.30 |
| Xanthan gum | 0.20 |
| Laureth-7 | 0.10 |
| Tetrasodium EDTA | 0.10 |
| Methylparaben | 0.09 |
| Butylparaben | 0.02 |
| Ethylparaben | 0.02 |
| Propylparaben | 0.01 |
| Isobutylparaben | 0.01 |
| Water qsp | to 100 |

A panel of 20 women applied the skin cream once daily during a period of 8 weeks on the back of one hand, while the other hand remained untreated.

The change in melanisation was measured with D-squam strips and subsequent microscopic observation (density of melanin in corneocytes). Skin depigmentation of age spots was objectively evaluated using a spectrocolorimeter before and after 8 weeks of treatment (L*-value).

After 8 weeks the dermatologist noticed an improvement of skin hydration of the treated hands i.e., softer and smoother skin compared with the dry to very dry untreated skin, indicating that the skin cream is a hydrating product.

A reduced density of melanin in the corneocyte cytoplasma or depigmentation activity was noted in 82% of the treated volunteers.

Figure 3:
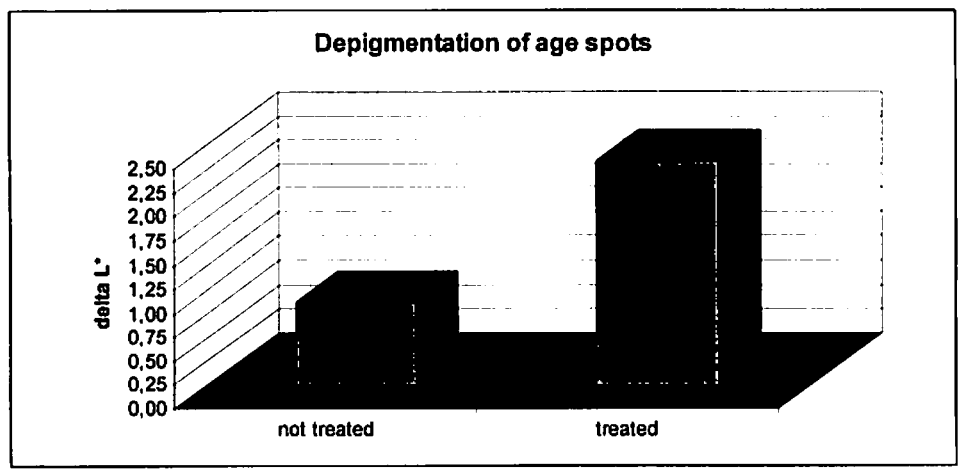
FIG. 3 illustrates the effect on age spots on skin as detailed in Example 2.

After 8 weeks, the age spots of the treated skin became more then 2 degrees lighter. The results are shown in FIG. 3.

A tendency was noted towards a brightness of the age spots in 72% of the treated volunteers.

Example 3

Assessment of Activity on Skin Structure

An objective measurement was carried out on the impact of cocoa polyphenols and cocoa butter on skin wrinkles and measurement of the skin tolerance.

Abdominal skin was used from a 68-year old Caucasian female.

Histological analysis was performed on day 0, 5 and 12. The following effects were assessed:
  Morphological analysis of the epidermis and dermis
  Visualisation of glycosaminoglycanes (GAG)
  Analysis of Collagen I, III and IV via immunostaining
  Analysis tolerance/irritation
  The following tests were set up:
  Skin without any treatment
  Skin receiving 0.5% cocoa extract in a water medium
  Skin receiving on the surface 2 mg cocoa butter
  Skin receiving on the surface 2 mg cocoa butter containing 1.5% cocoa extract
  Skin receiving 0.5% cocoa extract in a water medium and on the surface 2 mg cocoa butter containing 1.5% cocoa extract After 12 days, the dermatologist noticed an increased thickness of the epidermal layer, an increase in GAG presence, an increase in Collagen I, an increase in Collagen III, an increase in Collagen IV and good tolerance on the skin, indicating no irritation.

Figure 4A:
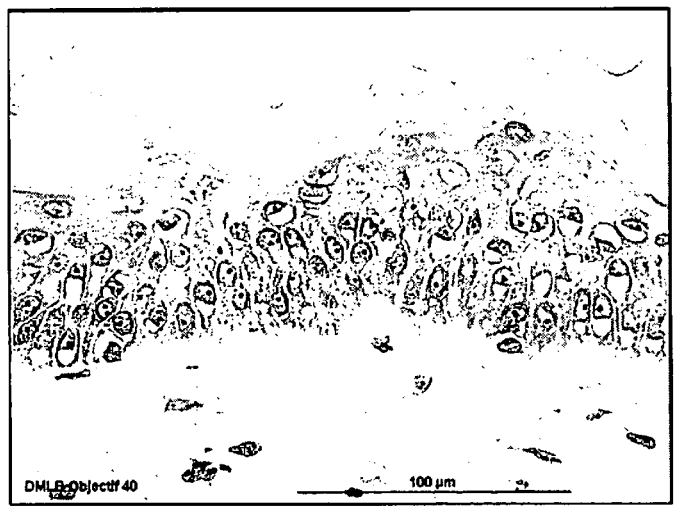
FIG. 4 illustrates the effect on skin morphology as detailed in Example 2.
Figure 4B:
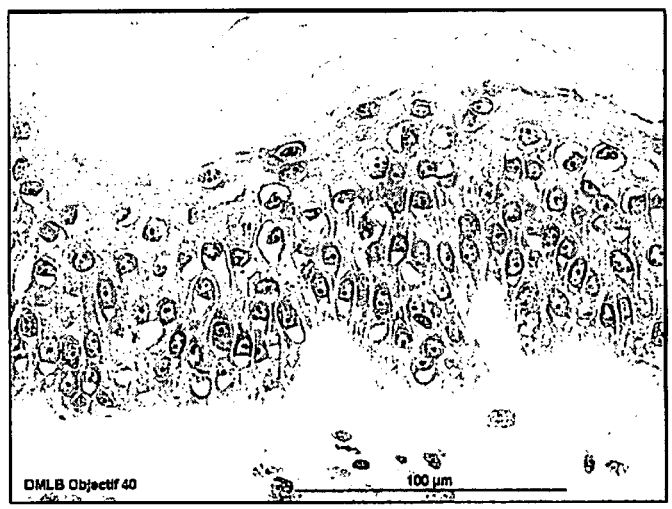
Figure 4C:
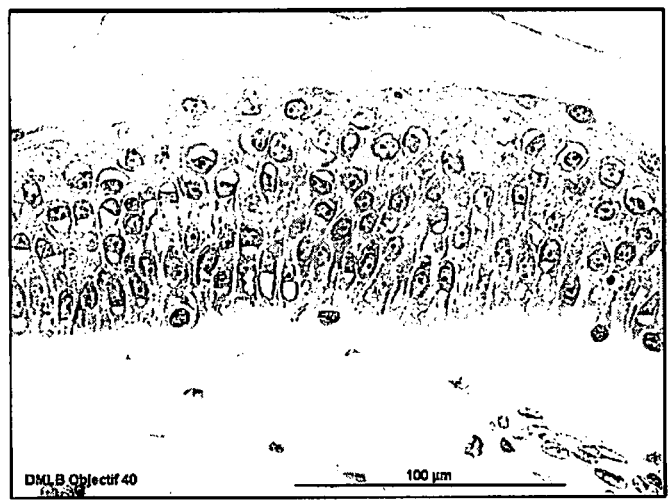

The effect on skin morphology at 5 days is shown in FIGS. 4A (untreated skin), 4B (cocoa butter alone) and 4C (combined cocoa butter and cocoa polyphenol extract).

The results show that skin treatment with cocoa butter improves the skin thickness in the epidermis and dermis by improving the growth of new skin cells. Skin treatment with cocoa butter in combination with cocoa polyphenols improves the skin thickness and elasticity by improving not only the growth of new cells, but also by increasing the collagen content in the dermis.

Example 4

Determination of Dose

The effect was determined of a skin cream containing cocoa polyphenols and cocoa butter on skin wrinkles.

Abdominal skin from a 43-year old Caucasian female was used. Different cocoa polyphenol concentrations were applied in combination with cocoa butter.

Histological analysis was performed on day 0, 6 and 11. The following effects were assessed:
  The morphology analysis of the epidermis and dermis
  Visualisation of glycosaminoglycans (GAG)
  Analysis of Collagen I, III and IV via immunostaining
  Analysis tolerance/irritation
  Image analysis
  The following tests were set up:
  Skin without any treatment
  Skin receiving on the surface 2 mg cocoa butter
  Skin receiving on the surface 2 mg cocoa butter containing 0.125% or 0.25% or 0.5% or 0.75% or 1.0% cocoa extract
  Skin receiving on the surface 2 mg commercially available products with anti-wrinkle activity After 11 days, the dermatologist noticed for the skin treated with cocoa polyphenols at a concentration of 0.5% and/or 0.75% in combination with cocoa butter: an increased thickness of the epidermal layer of about 40%; an increase in GAG (+200%) implying higher cell renewal; an increase in Collagen I (+100%); an increase in Collagen III (+50%) indicating more elastic skin; an increase in Collagen IV (+50%); and good tolerance on the skin. These two samples gave the best results and indicate a significant positive impact on wrinkles.

After 11 days, the cocoa product had significant benefits compared to existing products.

Image analysis was performed on immunostained pictures to have objective results for comparison. The results were as follows:

| % | Untreated skin | 0.75% cocoa extract in cocoa butter | 0.5% cocoa extract in cocoa butter | Commercial product |
|---|---|---|---|---|
| GAG | 15.5 | 46.3 | 38.1 | 34.2 |
|  | 100 | 299 | 246 | 221 |
| Collagen I | 20.7 | 41.2 | 28.4 | 17.4 |
|  | 100 | 199 | 137 | 84 |
| Collagen Iii | 31.7 | 38.9 | 50.9 | 47.2 |
|  | 100 | 123 | 161 | 149 |
| Collagen IV | 20.1 | 29.5 | 32 | 26.1 |
|  | 100 | 147 | 159 | 130 |

Figures in bold font in the table are absolute amounts present in the skin.
Figures in normal font are the relative amounts.

The invention claimed is:

1. A method for creating a skin anti-wrinkle effect comprising topically applying a composition to the skin, wherein the composition comprises: a cocoa polyphenol extract in combination with cocoa butter, wherein the cocoa polyphenol extract is obtained by the extraction of non-defatted cocoa beans which have not been fermented or have been allowed to ferment for no more than three days, and a cosmetically acceptable carrier, and wherein the cocoa polyphenol extract is present in an amount of from 0.1 to 13% by weight based on the weight of cocoa butter.

2. The method according to claim, wherein the cocoa polyphenol extract is present in an amount of from 8 to 12% by weight based on the weight of the cocoa butter.

3. The method according to claim 1, wherein the cocoa polyphenol extract is present in an amount of from 0.1 to 1% by weight based on the weight of the cocoa butter.

4. The method according to claim 1, wherein the cocoa polyphenol extract has a polyphenol content of at least 30% by weight.

5. The method according to claim 1, wherein the cocoa polyphenol extract has a polyphenol content of at least 40% by weight.

6. The method according to claim 1, wherein the cocoa polyphenol extract has a theobromine content of less than 5% by weight.

7. The method according to claim 1, wherein the cocoa polyphenol extract is obtained by solvent extraction of cocoa beans.

8. The method according to claim 7, wherein the solvent is selected from C1 to C6 alcohols or ketones, and mixtures thereof, optionally in admixture with water.

9. The method according to claim 1, wherein the cocoa polyphenol extract comprises from 0.1 to 10% by weight of cocoa fats.

* * * * *

UNITED STATES PATENT AND TRADEMARK OFFICE
CERTIFICATE OF CORRECTION

PATENT NO. : 8,637,093 B2  
APPLICATION NO. : 12/907347  
DATED : January 28, 2014  
INVENTOR(S) : Bernaert et al.

Page 1 of 1

It is certified that error appears in the above-identified patent and that said Letters Patent is hereby corrected as shown below:

In the Claims

Please replace:

"according to claim," in column 13, line 13 with "according to claim 1,"

Signed and Sealed this
Fourteenth Day of October, 2014

Michelle K. Lee
*Deputy Director of the United States Patent and Trademark Office*